United States Patent [19]

Dutzmann et al.

[11] Patent Number: 5,126,360
[45] Date of Patent: Jun. 30, 1992

[54] FUNGICIDAL ACTIVE COMPOUND COMBINATIONS

[75] Inventors: Stefan Dutzmann, Duesseldorf; Wilhelm Brandes, Leichlingen; Dieter Berg; Graham Holmwood, both of Wuppertal, all of Fed. Rep. of Germany

[73] Assignee: Bayer Aktiengesellschaft, Leverkusen, Fed. Rep. of Germany

[21] Appl. No.: 639,473

[22] Filed: Jan. 10, 1991

[30] Foreign Application Priority Data

Jan. 17, 1990 [DE] Fed. Rep. of Germany ....... 4001115

[51] Int. Cl.$^5$ .................. A01N 33/02; A01N 37/52; A01N 43/64
[52] U.S. Cl. .................. 514/383; 514/634; 514/636; 514/673; 514/674
[58] Field of Search ............... 514/383, 673, 674, 634, 514/636

[56] References Cited

U.S. PATENT DOCUMENTS 4,723,984  2/1988  Holmwood et al. ............... 71/76

FOREIGN PATENT DOCUMENTS 0052424  5/1982  European Pat. Off. .
0155509  9/1985  European Pat. Off. .
0266048  5/1988  European Pat. Off. .
55-139346 10/1980  Japan .
1570517  7/1980  United Kingdom .

OTHER PUBLICATIONS

Farm Chemicals Handbook, '89, Pesticide Dictionary, "Guazatine", p. C 151.

Primary Examiner—Allen J. Robinson
Attorney, Agent, or Firm—Sprung, Horn, Kramer & Woods

[57] ABSTRACT

A fungicidal composition comprising
A) 1-(4-chlorophenyl)-4,4-dimethyl-3-(1,2,4-triazol-1-yl-methyl)-pentan-3-ol of the formula

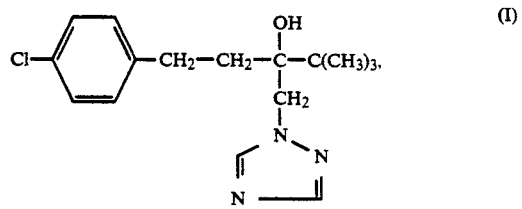

and
B) at least one guanidated aliphatic polyamine of the formula $$X^1-NH-R^1+N-R^2\nolimits_{\overline{n}}NH-X^3 \quad (II)$$
$$\phantom{X^1-NH-R^1}\,\,|\phantom{-R^2}$$
$$\phantom{X^1-NH-R^1}X^2$$

in which
$R^1$ represents a branched or unbranched, divalent aliphatic hydrocarbon radical having 3 to 14 carbon atoms,
$R^2$ represents a branched or unbranched, divalent aliphatic hydrocarbon radical having 3 to 14 carbon atoms,
$X^1$, $X^2$ and $X^3$ independently of one another represent hydrogen or the radical of the formula

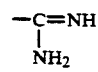

and
n represents integers from 0 to 16, it being possible for the divalent aliphatic hydrocarbon radicals which represents $R^2$ to be different from one another if n represents numbers larger than 1, or their acid addition salts.

3 Claims, No Drawings

FUNGICIDAL ACTIVE COMPOUND COMBINATIONS

The present invention relates to new active compound combinations which are very suitable for combating fungi and which consist, on the one hand, of 1-(4-chlorophenyl)-4,4-dimethyl-3-(1,2,4-triazol-1-yl-methyl)-pentan-3-ol, which is known, and, on the other hand, of guanidated aliphatic polyamines, which are likewise known.

It has already been disclosed that 1-(4-chlorophenyl)-4,4-dimethyl-3-(1,2,4-triazol-1-yl-methyl)-pentan-3-ol has a fungicidal potency (cf. EP-OS (European Published Specification) 0,040,345). The activity of this substance is good; however, at low application rates it leaves something to be desired in some cases.

It is furthermore already known that guanidated aliphatic polyamines have fungicidal properties. For example, the product with the common name "guazatine" can be employed for combating fungi (cf. K. H. Büchel "Pflanzenschutz und Schüdlingsbekümpfung [Plant Protection and Pest Control]", page 149, Georg Thieme Verlag, Stuttgart, 1977). However, the action of this substance is likewise not always satisfactory at low application rates.

It has now been found that the new active compound combinations of

A) 1-(4-chlorophenyl)-4,4-dimethyl-3-(1,2,4-triazol-1-yl-methyl)-pentan-3-ol, of the formula

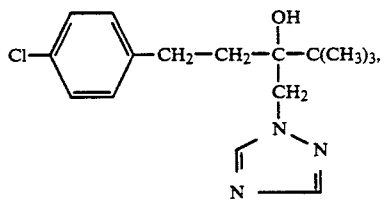

and

B) at least one quanidated aliphatic polyamine of the formula

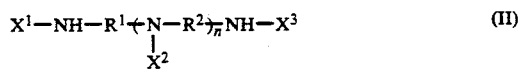

in which
R$^1$ represents a branched or unbranched, divalent aliphatic hydrocarbon radical having 3 to 14 carbon atoms,
R$^2$ represents a branched or unbranched, divalent aliphatic hydrocarbon radical having 3 to 14 carbon atoms,
X$^1$, X$^2$ and X$^3$ independently of one another represent hydrogen or the radical of the formula

—C=NH
|
NH$_2$ and
n represents integers from 0 to 16, it being possible for the divalent aliphatic hydrocarbon radicals which represent R$^2$ to be different from one another if n represents numbers larger than 1, and/or their acid addition salts have very good fungicidal properties.

Surprisingly, the fungicidal action of the active compound combinations according to the invention is considerably more powerful than the sum of the actions of the individual active compounds. This means that there is a true synergistic effect which could not have been predicted, not only a complementary action.

1-(4-Chlorophenyl)-4,4-dimethyl-3-(1,2,4-triazol1-yl-methyl)-pentan-3-ol, which is contained in the active compound combinations according to the invention and has the formula (I), has already been disclosed (cf. EP-OS (European Published Specification) 0,040,345).

Formula (II) provides a general definition of the guanidated aliphatic polyamines furthermore contained in the active compound combinations according to the invention. Preferred compounds of the formula (II) are those in which
R$^1$ represents an unbranched alkylene chain having 8 to 14 carbon atoms,
R$^2$ represents an unbranched alkylene chain having 8 to 14 carbon atoms,
X$^1$, X$^2$ and X$^3$ independently of one another represent hydrogen or the radical of the formula

—C=NH,
|
NH$_2$ and
n represents integers from 0 to 5, it being possible for the alkylene chains representing R, to be different from one another if n represents numbers larger than 1.

Other preferred compounds are addition products of acids and those guanidated aliphatic polyamines of the formula (II) in which R$^1$, R$^2$, X$^1$, X$^2$, X$^3$ and n have the meanings mentioned as preferred. The acids which can be added on preferably include hydrohalic acids such as hydrochloric acid and hydrobromic acid, in particular hydrochloric acid, furthermore phosphoric acid, nitric acid, sulphuric acid, carbonic acid, mono- and bifunctional carboxylic acids and hydroxycarboxylic acids such as formic acid, acetic acid, maleic acid, succinic acid, fumaric acid, oxalic acid, tartaric acid, citric acid, salicylic acid, sorbic acid and lactic acid, and furthermore arylsulphonic acids and alkylarylsulphonic acids having 1 to 25 carbon atoms, preferably 1 to 20 carbon atoms, in the alkyl moiety, p-toluenesulphonic acid and 4-(n-dodecyl)-benzenesulphonic acid being specifically mentioned.

Guanidated aliphatic polyamines of the formula (II) which can particularly preferably be used are the fungicides known under the common names "guazatine" and "iminoctadine" as well as their addition salts with acetic acid or 4-(n-dodecyl)-benzenesulfonic acid.

The fungicide with the common name "guazatine" is a product which is formed in the reaction of polyamines, in particular of octamethylenediamine, iminodi-(octa-methylene)-diamine and octamethylene-bis-(imino-octa-methylene)-diamine, with cyanamide and which is present in the form of acetate salts. The chemical composition of this product can be represented by the following formula:

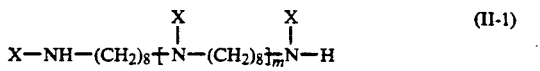

$$x (2 + m) CH_3COOH$$

where
m represents integers from 0 to 5 and p0 X represents hydrogen (17 to 23%) or the radical of

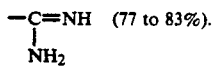 (77 to 83%).

Information on the composition of guazatine can also be found in Farm Chemicals Handbook 1989, C 151.

The fungicide with the common name "iminoctadine" is a product which is formed in the reaction of imino-bis-(8-amino-octyl), of the formula

with O-alkyl-isourea.

the active compound combinations according to the invention can contain one or more compounds of the formula (II) and/or their acid addition salts. If mixtures of compounds of the formula (II) are employed, than mixtures in which at least 70% of the radicals $X^1$, $X^2$ and $X^3$ represent a group of the formula

are preferred.

The guanidated aliphatic polyamines of formula (II) and their acid addition salts having already been disclosed (cf. GB-PS (British Patent Specification) 1,114,155, GB-PS (British Patent Specification) 1,570,517, EP-OS (European Published Specification) 0,155,509, JP-OS (Japanese Published Specification) 55-139,346 and K. H. Büchel "Pflanzenschutz and Schädlingsbekämpfung [Plant Protection and Pest Control]", page 149, Ceorg Thieme Verlag, Stuttgart, 1977).

The synergistic effect is particularly obvious if the active compounds are present in the active compound combinations according to the invention in certain ratios by weight. However, the ratios by weight of the active compounds in the active compound combinations can be varied within a relatively broad range. In general, 0.2 to 20 parts by weight, preferably 0.5 to 10 parts by weight, of guanidated aliphatic polyamines of the formula (II) are used per part by weight of active compound of the formula (I).

The active compound combinations according to the invention have very good fungicidal properties and can be employed for combating phytopathogenic fungi such as Plasmodiophoromycetes, Oomycetes, Chytridiomycetes, Zygomycetes, Ascomycetes, Basidiomycetes, Deuteromycetes, etc.

The active compound combinations according to the invention are particularly well suited for combating Botrytis species in viticulture, in soft fruit and in vegetable growing, and for combating cereal diseases such as Fusarium.

The good toleration by plants of the active compound combinations in the concentrations required for combating plant diseases permits treatment of aerial parts of plants, of vegetative propagation stock and seed, and of the soil.

The active compound combinations according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds, or the active compound combinations, with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin nydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight f active compounds, preferably between 0.5 and 90%.

The active compound combinations according to the invention can be present in the formulations as a mixture with other known active compounds, such as fungicides. insecticides, acaricides and herbicides, as well as in mixtures with fertilizers and plant growth regulators.

The active compound combinations can be used as such. in the form of their formulations or the use forms prepared therefrom, such as ready-to-use solutions, emulsifiable concentrates, emulsions, suspensions, wettable powders, soluble powders and granules. They are used in the customary manner, for example by watering, spraying, atomizing, scattering, brushing on, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g. are generally required.

For the treatment of soil, active compound concentrations of 0.00001 to 0.1% by weight, preferably of 0.0001 to 0.02% by weight, are required at the place of action.

The good fungicidal action of the active compound combinations according to the invention can be seen from the example which follows. While the individual active compounds show weak points in the fungicidal action, the combination has an action which transcends the simple sum of actions.

A synergistic effect in fungicides is always present if the fungicidal action of the active compound combinations is larger than the sum of the actions of the individually applied active compounds.

EXAMPLE 1

Fusarium Nivale Test (Rye)/Seed Treatment

The active compounds are applied as dry-dressing agents. They are prepared by extending the particular active compound, or the active compound combination, with ground rock to give a finely pulverulent mixture which guarantees uniform distribution on the seed surface.

To carry out the treatment, the infected seeds and the seed-dressing agent are shaken for 3 minutes in a sealed glass flask.

2×100 rye grains are sown in standard soil to a depth of 1 cm, and the rye is grown in a greenhouse at a temperature of about 10° C. and a relative atmospheric humidity of about 95% in seed boxes which are exposed to light for 15 hours per day.

3 weeks after sowing, the plants are evaluated for snow mold symptoms.

The active compounds, active compound concentrations and test results can be seen from the table below.

TABLE 1

| Fusarium nivale test Active compound | (rye)/seed treatment | |
|---|---|---|
| | Application rate of active compound in mg/kg of seed | Degree of effectiveness in % relative to the untreated control |
| Untreated | — | = 0 |
| known: | | |
| 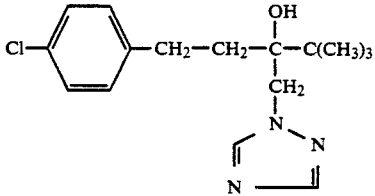 (I) | 80 <br> 10 | 24 <br> 33 |
| (II-1) guazatine | 80 <br> 10 | 93 <br> 29 |
| according to the invention: | | |
| (I) + (II-1) guazatine (1:7) | 10 + 70 | 100 |
| (I) + (II-1) guazatine (1:1) | 5 + 5 | 60 |

It will be appreciated that the instant specification is set forth by way of illustration and not limitation, and that various modifications and changes may be made without departing from the spirit and scope of the present invention.

What is claimed is:

1. A fungicidal composition comprising a synergistic fungicidially effective amounts of the mixture of:
   A) 1-4-chlorophenyl)-4,4-dimethyl-3-(1,2,4-triazol-1-yl-methyl)-pentan-3-ol of the formula

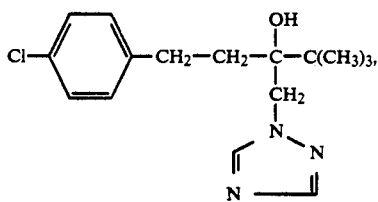 (I)

and

B) at least one guanidated aliphatic polyamide of the formula

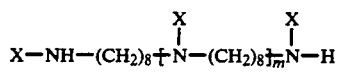 (II-1)

x (2 + m) CH₃COOH where
m represents integers from 0 to 5 and
X represents hydroen (17 to 23%) or the radical of the formula $$-\underset{NH_2}{\underset{|}{C}}=NH \quad (77 \text{ to } 83\%)$$

wherein the synergistic ratio by weight of A to B is from about 1:0,2 to 1:20.

2. The composition of claim 1 wherein the synergistic weight ratio of A to B is from about 1:0.5 to 1:10.

3. A method of combating fungi which comprises applying to such fungi or to a locus from which it is desired to exclude fungi a synergistic fungicidally effective amount of a composition according to claim 1.

* * * * *